United States Patent [19]

Horn et al.

[11] Patent Number: 4,726,955

[45] Date of Patent: Feb. 23, 1988

[54] PREPARATION OF FINELY DIVIDED, PULVERULENT CAROTENOID PREPARATIONS

[75] Inventors: Dieter Horn, Heidelberg; Hans-Juergen Quadbeck-Seeger, Bad Durkheim; Peter Schaefer, Kirchheim; Wolfgang Haehnlein, Friedelsheim, all of Fed. Rep. of Germany

[73] Assignee: BASF Aktiengesellschaft, Ludwigshafen, Fed. Rep. of Germany

[21] Appl. No.: 29,808

[22] Filed: Mar. 25, 1987

[30] Foreign Application Priority Data

Apr. 4, 1986 [DE] Fed. Rep. of Germany ....... 3611229

[51] Int. Cl.$^4$ .................... A23L 1/275; A23L 1/303; B01J 13/00
[52] U.S. Cl. ...................................... 426/73; 426/540; 426/96; 426/98; 252/311; 252/306; 252/312
[58] Field of Search ..................... 426/73, 540, 96, 98; 252/311, 306, 312; 424/341

[56] References Cited

U.S. PATENT DOCUMENTS

| | | | |
|---|---|---|---|
| 2,282,789 | 5/1942 | Musher | 426/73 |
| 3,110,598 | 11/1963 | Müller et al. | 426/540 |
| 3,125,451 | 3/1964 | Wingerd et al. | 426/540 |
| 3,655,406 | 4/1972 | Klaui | 426/540 |
| 3,734,745 | 5/1973 | Cassanelli | 426/540 |
| 4,522,743 | 6/1985 | Horn et al. | 426/73 |

FOREIGN PATENT DOCUMENTS 0065193 11/1982 European Pat. Off. .

*Primary Examiner*—Jeanette Hunter
*Attorney, Agent, or Firm*—Keil & Weinkauf

[57] ABSTRACT

Finely divided, pulverulent carotenoid preparations in which the carotenoid essentially has a particle size of less than 0.5 micron are prepared by a process in which a carotenoid is dissolved in a volatile, water-miscible, organic solvent at from 50° to 240° C., under atmospheric or superatmospheric pressure, in less than 10 seconds, the carotenoid is precipitated in colloidal disperse form from the resulting molecular disperse solution by rapid mixing with milk at from 0° to 50° C., and the resulting dispersion is freed from the solvent and the dispersing medium in a conventional manner.

4 Claims, 1 Drawing Figure

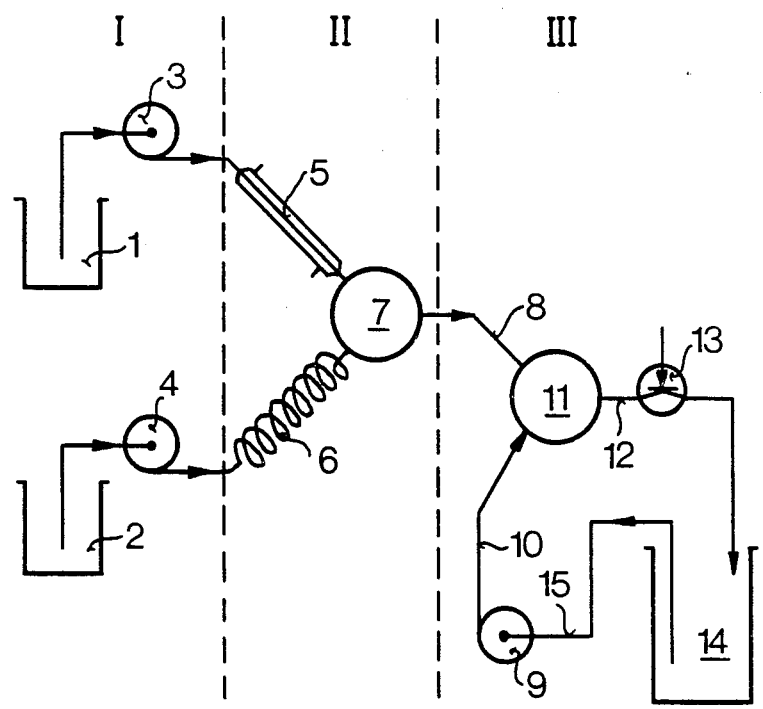

PREPARATION OF FINELY DIVIDED, PULVERULENT CAROTENOID PREPARATIONS

The present invention relates to a process for the conversion of carotenoids to a finely divided, pulverulent form which is required in particular for coloring food and animal feeds.

The carotenoids constitute a group of colored pigments which have hues from yellow to red, are widespread in nature and in part a characteristic color to many foods. Important members of this class of substances are β-carotene, β-apo-8'-carotenal, canthaxanthin and citranaxanthin. These substances which can be synthesized are important colorants both for the foodstuffs and animal feeds industry and for pharmaceutical technology, for example as a substitute for artificial colorants, or are of interest, for example, because of their provitamin A activity.

All carotenoids are insoluble in water and are also only slightly soluble in fats and oils. This limited solubility and the high sensitivity to oxidation prevent the relatively coarse-particled products contained in the synthesis from being used directly for coloring food or animal feeds, since only a low color yield can be achieved and the substances in the coarsely crystalline form are poorly absorbed. These effects which are disadvantageous with regard to using the carotenoids in practice are felt in particular in an aqueous medium since they are completely insoluble therein.

Various methods have been described for improving the color yield and increasing the absorption, the object of all of these methods being to reduce the crystallite size of the active ingredients and bring it to a particle size range of less than 10 μm. For example, according to Chimia 21 (1967), 329, β-carotene can be milled together with edible oil under a nitrogen atmosphere in a colloid mill to a particle size of from 2 to 5 μm. According to Food Technol. 12 (1958), 527, the oil coating also protects the active ingredient from oxidation. The suspension which is obtained in this manner and contains up to 20 or 30% of active ingredient can be successfully used for coloring fats and oils since the solubility, although low, is sufficient to bring the crystallites into solution and the low concentration usually employed.

On the other hand, conditioning the active ingredients for use in an aqueous medium is much more difficult. The carotenoids have no detectable solubility in aqueous media, and the desired coloring and absorption properties can only be achieved by means of a very finely divided crystalline state. A particle size of less than 1 μm is desirable, but this either cannot be achieved at all by milling or can be achieved only with damage to the active ingredient. Attempts to dissolve the carotenoids using a water-soluble organic solubilizer, such as an alcohol or acetone, and then to precipitate them in finely crystalline form by dilution with water have been unsuccessful to date owing to the excessively low solubility of the carotenoids in these solvents. For example, the solubility of β-carotene at room temperature in acetone is less than 0.1% by weight, and that in ethanol is less than 0.01% by weight.

Other processes for producing a preparation containing finely divided active ingredients are based on the application of these active ingredients onto carriers, such as starch, pectin or dried milk powder, for example a solution of the active ingredient in oil, as described in German Patent No. 642,307, or in chloroform, as described in German Patent No. 861,637 and Swiss Patent No. 304,023, being sprayed onto the carriers. However, the resulting preparations are not universally dispersable in aqueous media and do not meet the usual requirements in respect of shelf life since the active ingredients which accumulate at the surface are rapidly destroyed by oxidation. Finally, processes may also be mentioned in which active ingredients in the form of their solutions in oil are embedded in colloids, such as gelatine, to form emulsions, as described in Chimia 21 (1967), 329 and in French Patent No. 1,056,114 and U.S. Pat. No. 2,650,895. However, owing to the low solubility of the active ingredients in oil, the concentrations of the said ingredients in the resulting preparations are low.

On the other hand, known processes in which the active ingredient is dissolved in a water-immiscible solvent, preferably a chlorohydrocarbon, such as chloroform or methylene chloride, the solution is emulsified by homogenization in a gelatine/sugar solution, and finally the solvent is stripped off from the emulsion, the active ingredient being liberated in finely crystalline form, constitute a certain advance. A process of this type is described in Chimia 21 (1967), 329 and in German Published Application DAS No. 1,211,911 and German Laid-Open Application DOS No. 2,534,091. A finely divided powder is then obtained from the resulting suspension by removal of water.

However, this process has the disadvantage that chlorohydrocarbons have to be used in order to obtain a sufficiently high concentration of active ingredient in the emulsion phase. Complete removal of the chlorohydrocarbons, which is necessary for toxicological reasons, is technically difficult.

The stated disadvantages were overcome by the process described in European Patent No. 65,193, in which, in order to prepare finely divided, pulverulent carotenoid preparations, particularly for coloring food and animal feeds, a carotenoid was dissolved in a volatile, water-miscible organic solvent at from 50° to 240° C., under atmospheric or superatmospheric pressure in less than 10 seconds, the carotenoid was precipitated immediately in colloidal form from the resulting molecular disperse solution by rapid mixing with an aqueous solution of a swellable colloid at from 0° to 50° C., and the resulting dispersion was freed from the solvent and the dispersing medium in a conventional manner.

We have found, surprisingly, that milk or skimmed milk can advantageously be used instead of the swellable colloid.

Milk is understood as meaning, in particular, full-fat cow's milk, and skimmed milk is understood as meaning partially or completely skimmed milk. The milk may furthermore be diluted with up to five times the amount of water or may contain further additives. Reconstituted milk produced from milk powder may also be used.

The possibility of using milk was surprising for several reasons:
1. It is known that milk is denatured (coagulated) by the addition of alcohol, the highly pH-dependent limiting concentration decreasing in the order methanol, ethanol and propanol. Acetone is known to be similar (cf. for example D. S. Horne and T. G. Parker, Int. J. Biol. Macromol. 3 (1981), 300.
2. It is also known that milk can be caused to coagulate by the action of heat, the coagulation times being highly temperature-dependent and decreasing with increasing temperature (cf. E. Dickinson and G.

Stainsby, Colloids in Food, Applied Science Publishers, London, 1982, page 449 et seq).

3. A combination of the two effects, as is present in our process, would therefore be expected to result in a substantial increase in the tendency to undergo denaturing.

4. It is clear to the skilled worker that a denatured, i.e. coagulated, milk protein system cannot effect colloidal stabilization of a microdisperse system, such stabilization being a precondition for the success of the present process. It is therefore surprising that, even at process temperatures of 200° C., the process involving preparation of a finely divided product takes place without problems and gives a microdisperse active ingredient which, after the solvent has been stripped off, for example by distillation, can be converted in a conventional manner, for example by spray drying, to a powder formulation.

The carotenoids which can be used in carrying out the invention are the known, accessible, natural or synthetic members of this class of compounds which can be used as color-imparting agents, for example carotene, lycopene, bixin, zeaxanthin, cryptoxanthin, citranaxanthin, lutein, canthaxanthin, astaxanthin, β-apo-4'-carotenal, β-apo-8'-carotenal, β-apo-12'-carotenal, β-apo-8'carotenic acid and esters of hydroxyl-containing and carboxyl-containing members of this group, for example the lower alkyl esters, preferably the methyl and ethyl esters. The members which have been readily available industrially to date, such as β-carotene, canthaxanthin, β-apo-8'-carotenal and β-apo-8'-carotenates, are particularly preferred.

Water-miscible, thermally stable, volatile solvents containing only carbon, hydrogen and oxygen, such as alcohols, ethers, esters, ketones and acetals, are particularly suitable for carrying out the novel process. Ethanol, n-propanol, isopropanol, butane-1,2-diol 1-methyl ether, propane-1,2-diol 1-n-propyl ether or acetone are preferably used.

In general, solvents which exhibit not less than 10% miscibility with water, have a boiling point of less than 200° C. and/or possess less than 10 carbon atoms are advantageously used.

To increase the stability of the active ingredient to oxidative degradation, it is advantageous to add stabilizers, such as α-tocopherol, lecithin, tert-butylhydroxytoluene, tert-butylhydroxyanisole or ethoxyquine. They may be added either to the milk or to the solvent phase but are preferably dissolved, together with the colorants and the surfactant-like stabilizers, in the solvent phase. In certain circumstances, it may also be advantageous to dissolve oil or a solid in the solvent phase, this oil or solid then being precipitated in extremely finely divided form together with the active ingredient and the stated additives during mixing with the the aqueous phase. A viscous liquid having a deep color is obtained, from which the solvent, depending on its boiling point, can be removed in a conventional manner, for example by distillation, under atmospheric or reduced pressure, or by extraction with a water-immiscible solvent. However, the solvent is preferably removed together with the water by spray drying or spray granulation.

The resulting dry powder can be redissolved in water, the active ingredient being obtained in a uniformly finely divided form and having a particle size of less than 1 μm. In spite of the fact that it is finely divided, the resulting hydrosol of the active ingredient proves extremely stable in the photochemical stability test.

Alternatively, the micronized active ingredient, after being brought to a suitable pH, can also be flocculated together with the milk colloids and thus converted to a form from which the solvent and a major part of the dispersing medium can be separated off by filtration or centrifuging in a simple manner. The coacervate thus obtained is then dried in a conventional manner and converted to granules.

Specifically, the novel process is carried out, for example, using an apparatus as shown schematically in FIG. 1, the procedure being as follows.

The apparatus consists of parts I, II and III. Part II is the high temperature section, while the temperatures in parts I and III are less than 50° C.

A suspension of the carotenoid in the selected solvent, in a concentration of from 2 to 20% by weight, based on the mixture, with or without the addition from 0.1 to 10% by weight of stabilizers, is initially taken in vessel (1). Vessel (2) containing the solvent without any admixed carotenoid. The suspension of the active ingredient, and the solvent, are fed to mixing chamber (7) by means of pumps (3) and (4), the ratio of the components in the mixture being predetermined by the choice of the particular deliveries of the pumps and being selected so that, depending on the solvent and the residence time, the resulting carotenoid concentration in the mixing chamber is from 0.5 to 10% by weight, based on the solution. The volume of the mixing chamber (7) is such that, at the selected deliveries of pumps (3) and (4), the residence time in (7) is preferably less than 1 second.

Before entering the mixing chamber, the solvent is brought to the desired temperature by means of heat exchanger (6), while the suspension of active ingredient is kept at temperatures above 50° C. by feeding it in via the thermally insulated feed line (5). The active ingredient is dissolved at from 50° to 240° C., preferably from 150° to 200° C., by turbulent mixing in (7), and, after a short residence time, preferably less than 1 second, the resulting solution passes via (8) into the second mixing chamber (11), in which the active ingredient is precipitated in colloidal disperse form by mixing with milk via pump (9) and feed line (10). The finely divided dispersion of active ingredient is then discharged via line (12) and pressure control valve (13) and is fed to stock vessel (14). In order to achieve a very high concentration of active ingredient, the dispersion can be circulated via suction line (15).

If the pressure control valve (13) is set to pressures above one bar, solvents can even be used at temperatures above their boiling point (under atmospheric pressure) in the novel process.

The dispersion is converted to a pulverulent preparation in a conventional manner, for example as described in German Laid-Open Application DAS No. 2,534,091, by spray drying or spray cooling or by coating the particles, separating them off and drying them in a fluidized bed.

For spray drying, the dispersion is either first freed from the solvent by distillation, preferably under reduced pressure, or by extraction with a water-immiscible solvent, or the entire mixture is spray dried and the water and solvent thus stripped off together in the spray tower.

The carotenoid powder is obtained in a dry, freeflowing form at the bottom of the spray tower. In some cases, it may be advantageous additionally to carry out the entire drying procedure in a fluidized bed.

Instead of preparing the powder formulation by spray drying, it is also possible to use any other methods in order to convert the carotenoids, which are already in finely divided form in the water/solvent dispersion, into the powder form.

The Examples which follow illustrate the process according to the invention.

EXAMPLE 1

20 g of trans-β-carotene are suspended in 240 g of a solution of 4 g of ascorbyl palmitate and 8 g of dl-α-tocopherol in 240 g of an isopropanol azeotrope (12% of water) and are mixed in mixing chamber (7) with 360 g of isopropanol azeotrope which has been heated to 230° C. in heat exchanger (6), the pressure control valve (13) being set at 25 bar. When the suspension is metered at a rate of 2 l/h and the solvent at a rate of 3 l/h, the residence time in the mixing chamber (7) is 0.35 second. The molecular disperse solution formed at 195° C. during this procedure is then fed to mixing chamber (11), where it is mixed with 4000 g of full milk (fat content 3.5%) at a flow rate of 27 l/h to precipitate the β-carotene in colloidal disperse form. A colloidal dispersion of active ingredient which has an orange-yellow hue and is at 50° C. is obtained in collecting vessel (14). Particle size analysis of the micronized product by quasielastic laser light scattering gives a mean particle size of 250 nm.

After the solvent has been separated off under reduced pressure at 50° C. in a distillation apparatus, a colloidal dispersion of active ingredient is obtained, and this dispersion can be converted to a stable, watersoluble dry powder by spray drying.

If the procedure described in Example 1 is followed but the following carotenoids or milk products are used, the results stated in Table 1 are obtained.

TABLE 1

| Example | Type of milk | Carotenoid | Content of active ingredient in the dry powder |
|---------|--------------|------------|-----------------------------------------------|
| 2 | Skimmed milk, 1.5% fat | β-carotene | 3.5% |
| 3 | Fully skimmed milk, 0.3% fat | " | 4.5% |
| 4 | Fully skimmed milk, but diluted | " | 10% |

TABLE 1-continued

| Example | Type of milk | Carotenoid | Content of active ingredient in the dry powder |
|---------|--------------|------------|-----------------------------------------------|
|  | with fully deionized water (1:2) |  |  |
| 5 | Fully skimmed milk, 0.3% | Canthaxanthin | 4.0% |
| 6 | Fully skimmed milk, 0.3% | 13-Z-vitamin-A acid | 3.5% |

EXAMPLE 7

The procedure described in Example 1 is followed, except that only 2000 g of full milk is used in mixing chamber (11) at a flow rate of 14 l/h. The content of active ingredient in the dry powder is 7%.

EXAMPLE 8

The procedure described in Example 1 is followed, except that 4000 g of a solution of 150 g of dry milk in distilled water is used in mixing chamber (11).

We claim:

1. A process for the preparation of a finely divided, pulverulent carotenoid preparation, in which the carotenoid essentially has a particle size of less than 0.5 micron, by dissolving a carotenoid in a volatile, water-miscible, organic solvent at from 50° to 240° C., under atmospheric or superatmospheric pressure, in less than 10 seconds, immediately precipitating the carotenoid in colloidal disperse form from the resulting molecular disperse solution by rapidly mixing with an aqueous dispersion of a colloid at from 0° to 50° C. and freeing the resulting dispersion from the solvent and the dispersing medium in a conventional manner, wherein the colloid used is milk or skimmed milk or an aqueous solution of dry milk.

2. A process for the preparation of a finely divided, pulverulent carotenoid preparation as claimed in claim 1, wherein the water-miscible volatile solvent used is an alcohol, a ketone, an ester, an acetal or an ether.

3. A process for the preparation of a carotenoid preparation as claimed in claim 2, wherein the water-miscible volatile solvent used is acetone, butane-1,2-diol 1-methyl ether, propane-1,2-diol 1-n-propyl ether ethanol, n-propanol, isopropanol or a mixture of these.

4. A process as claimed in claim 1, wherein the preparation of the molecular disperse carotenoid solution and the precipitation of the carotenoid in very finely disperse form are carried out continuously in two mixing chambers connected in series.

* * * * *